US008609921B1

(12) United States Patent
Nicholas et al.

(10) Patent No.: US 8,609,921 B1
(45) Date of Patent: Dec. 17, 2013

(54) AROMATIC TRANSALKYLATION USING UZM-44 ALUMINOSILICATE ZEOLITE

(71) Applicant: UOP LLC, Des Plaines, IL (US)

(72) Inventors: Christopher P. Nicholas, Evanston, IL (US); Edwin P. Boldingh, Arlington Heights, IL (US); Marc R. Schreier, Romeoville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/792,667

(22) Filed: Mar. 11, 2013

Related U.S. Application Data

(60) Provisional application No. 61/736,347, filed on Dec. 12, 2012.

(51) Int. Cl.
*C07C 6/12* (2006.01)
(52) U.S. Cl.
USPC ........................................................ 585/475
(58) Field of Classification Search
USPC ........................................................ 585/475
See application file for complete search history.

(56) References Cited

U.S. PATENT DOCUMENTS

| | | | |
|---|---|---|---|
| 2,620,314 A | 12/1952 | Hoekstra | |
| 2,948,675 A | 8/1960 | Case et al. | |
| 3,146,188 A | 8/1964 | Gossett | |
| 3,227,645 A | 1/1966 | Frumkin et al. | |
| 3,658,695 A | 4/1972 | VanPool | |
| 3,839,187 A | 10/1974 | Vanvenrooy | |
| 4,052,476 A * | 10/1977 | Morrison .................... | 585/471 |
| 4,197,192 A | 4/1980 | Gould | |
| 4,310,440 A | 1/1982 | Wilson et al. | |
| 4,354,928 A | 10/1982 | Audeh et al. | |
| 4,440,871 A | 4/1984 | Lok et al. | |
| 4,478,705 A | 10/1984 | Ganguli | |
| 4,483,691 A | 11/1984 | McShea, III et al. | |
| 4,645,589 A | 2/1987 | Krambeck et al. | |
| 4,870,222 A | 9/1989 | Bakas et al. | |
| 5,157,196 A | 10/1992 | Crossland et al. | |
| 5,157,197 A | 10/1992 | Cooper et al. | |
| 5,961,786 A | 10/1999 | Freel et al. | |
| 6,136,290 A | 10/2000 | Benazzi et al. | |
| 6,239,057 B1 | 5/2001 | Ichikawa et al. | |
| 6,426,442 B1 | 7/2002 | Ichikawa et al. | |
| 6,514,479 B1 | 2/2003 | Merlen et al. | |
| 6,613,302 B1 | 9/2003 | Moscoso et al. | |
| 6,627,781 B1 | 9/2003 | Briot et al. | |
| 6,740,788 B1 | 5/2004 | Maher et al. | |
| 6,756,030 B1 | 6/2004 | Rohde et al. | |
| 6,776,975 B2 | 8/2004 | Wilson et al. | |
| 7,374,662 B2 | 5/2008 | Duplan et al. | |
| 7,419,931 B2 | 9/2008 | Serra et al. | |
| 7,575,737 B1 | 8/2009 | Miller et al. | |
| 7,615,143 B2 | 11/2009 | Chen et al. | |
| 7,629,499 B2 | 12/2009 | Serra Alfaro et al. | |
| 7,687,423 B2 | 3/2010 | Moscoso et al. | |
| 7,713,513 B2 | 5/2010 | Jan et al. | |
| 7,982,083 B2 | 7/2011 | Guillon et al. | |
| 8,048,403 B2 | 11/2011 | Miller et al. | |
| 8,134,037 B2 | 3/2012 | Bogdan et al. | |
| 8,178,740 B2 | 5/2012 | Nicholas et al. | |
| 8,183,172 B2 | 5/2012 | Guillon et al. | |
| 8,263,032 B2 | 9/2012 | Andersen et al. | |
| 8,398,955 B2 | 3/2013 | Lai et al. | |
| 8,461,405 B2 | 6/2013 | Sanchez et al. | |
| 2008/0179221 A1 | 7/2008 | Nguyen et al. | |
| 2010/0144513 A1 | 6/2010 | Nicholas et al. | |
| 2010/0144514 A1 | 6/2010 | Nicholas et al. | |
| 2010/0298117 A1 | 11/2010 | Levin et al. | |
| 2011/0174692 A1 | 7/2011 | Negiz et al. | |
| 2011/0178354 A1 | 7/2011 | Negiz et al. | |
| 2011/0178356 A1 | 7/2011 | Negiz et al. | |
| 2012/0024752 A1 | 2/2012 | Chen et al. | |
| 2012/0029257 A1 | 2/2012 | Chen et al. | |
| 2012/0121568 A1 | 5/2012 | Chen et al. | |

FOREIGN PATENT DOCUMENTS

| | | |
|---|---|---|
| CA | 2268803 A1 | 4/1998 |
| CN | 102040459 | 5/2011 |
| DE | 69710612 | 11/2002 |
| GB | 682387 | 11/1952 |
| GB | 915601 | 1/1963 |
| JP | 11253810 | 9/1999 |
| JP | 4595106 | 12/2010 |

(Continued)

OTHER PUBLICATIONS

Hong et al., "Synthesis, Structure Solution, Characterization, and Catalytic Properties of TNU-10: A High-Silica Zeolite with the STI Topology", J. Am. Chem Society, 2004, vol. 126, pp. 5718-5826.
Gramm et al., "Complex zeolite structure solved by combining powder diffraction and electron microscopy", Nature, 2006, vol. 444, pp. 79-81.
Baerlocher et al., "Structure of Polycrystalline Zeolite Catalyst IM-5 Solved by Enhanced Charge Flipping", Science, 2007, vol. 315, pp. 1113-1116.
Rietveld, "A Profile Refinement Method for Nuclear and Magnetic Structures", Journal of Applied Crystallography, 1969, vol. 2, pp. 65-71.
Brunauer et al., "Adsorption of Gases in Multimolecular Layers", J. Am. Chem Society, 1938, vol. 60, pp. 309-319.

(Continued)

*Primary Examiner* — Thuan D Dang
(74) *Attorney, Agent, or Firm* — Maryann Maas

(57) ABSTRACT

A new family of aluminosilicate zeolites designated UZM-44 has been synthesized. These zeolites are represented by the empirical formula.

$$Na_nM_m^{k+}T_rAl_{1-x}E_xSi_yO_z$$

where M represents a metal or metals from zinc, Group 1, Group 2, Group 3 and or the lanthanide series of the periodic table, "m" is the mole ratio of M to (Al+E), T is the organic structure directing agent or agents, and E is a framework element such as gallium. UZM-44 may be used to catalyze a process for the transalkylation of a feedstream comprising one or more of $C_7$, $C_9$, $C_{10}$ and $C_{11}+$ aromatics to obtain a transalkylation product stream having an increased concentration of $C_8$ aromatics relative to that of the feedstream.

17 Claims, 4 Drawing Sheets

(56) References Cited

FOREIGN PATENT DOCUMENTS

| KR | 480229 | 3/2005 |
|---|---|---|
| KR | 2011047178 | 5/2011 |
| KR | 2012023156 | 3/2012 |
| KR | 1174099 | 8/2012 |
| KR | 2012091865 | 8/2012 |
| WO | 9817581 | 4/1998 |
| WO | 2012027034 A2 | 3/2012 |

OTHER PUBLICATIONS

Portilla et al., "Structure-reactivity relationship for aromatics transalkylation and isomerization process with TNU-9, MCM-22 and ZSM-5 zeolites, and their industrial implications", Applied Catalysis A: General, 2011, vol. 393, n 1-2, pp. 257-268.

Serra et al., "A rational design of alkyl-aromatics dealkylation-transalkylation catalysts using C8 and C9 alkyl-aromatics as reactants", Journal of Catalysis, 2004, vol. 227, n 2, pp. 459-469.

Cejka et al., "Novel zeolites in transformation of aromatic hydrocarbons", King Fahd University of Petroleum and Minerals—18th Annual Saudi-Japan Symposium on Catalysts in Petroleum Refining and Petrochemicals, Nov. 2008, pp. 117-126, Publisher: King Fahd Univ. of Petroleum and Minerals Res. Inst.

Bleken et al., "Conversion of methanol over 10-ring zeolites with differing volumes at channel intersections: Comparison of TNU-9, IM-5, ZSM-11 and ZSM-5w", Physical Chemistry Chemical Physics, 2011, vol. 13, n 7, pp. 2539-2549.

Odedairo et al., "Toluene disproportionation and methylation over zeolites TNU-9, SSZ-33, ZSM-5, and mordenite using different reactor systems", Industrial and Engineering Chemistry Research, 2011, vol. 50, n 6, pp. 3169-3183.

Corma et al., "IM-5: A highly thermal and hydrothermal shape-selective cracking zeolite", Journal of Catalysis, 2002, vol. 206, n 1, pp. 125-133.

Jae et al., "Production of green aromatics from catalytic fast pyrolysis of lignocellulosic biomass", 11AIChE—2011 AIChE Annual Meeting, Conference Proceedings, Oct. 16-21, 2011, Publisher: American Institute of Chemical Engineers.

Jae et al., "Investigation into the shape selectivity of zeolite catalysts for biomass conversion", Journal of Catalysis, 2011, vol. 279, n 2, pp. 257-268.

Tukur et al., "Comparison studies of xylene isomerization and disproportionation reactions between SSZ-33, TNU-9, mordenite and ZSM-5 zeolite catalysts", Chemical Engineering Journal, vol. 166, n 1, pp. 348-357, Jan. 1, 2011.

Hong et al., "Synthesis, crystal structure, characterization, and catalytic properties of TNU-9", Journal of the American Chemical Society, 2007, vol. 129, n 35, pp. 10870-10885.

Corma et al., "Determination of the pore topology of zeolite IM-5 by means of catalytic test reactions and hydrocarbon adsorption measurements", Journal of Catalysis, 2000, vol. 189, n 2, pp. 382-394.

Lee et al., "Synthesis, characterization, and catalytic properties of zeolites IM-5 and NU-88", Journal of Catalysis, 2003, vol. 215, n 1, pp. 151-170.

Palomares et al., "Co-exchanged IM5, a stable zeolite for the selective catalytic reduction of NO in the presence of water and SO2", Industrial and Engineering Chemistry Research, 2003, vol. 42, n 8, pp. 1538-1542.

He et al., "A theoretical study of the stability of Cu2+ ion in IM-5 zeolite and the interaction of Cu-IM-5 with NO", Microporous and Mesoporous Materials, 2009, vol. 121, n 1-3, pp. 95-102.

Liu et al., "Synthesis of Mo/TNU-9 (TNU-9 Taejon National University No. 9) catalyst and its catalytic performance in methane non-oxidative aromatization", Energy, 2011, vol. 36, n 3, pp. 1582-1589.

Liu et al., "Synthesis of Mo/IM-5 catalyst and its catalytic behavior in methane non-oxidative aromatization", Fuel, 2011, vol. 90, n 4, pp. 1515-1521.

Li et al., "Deep oxidative desulfurization of fuels in redox ionic liquids based on iron chloride", Green Chemistry, 2009, vol. 11, pp. 810-815.

Feng et al., "Application of phosphate ionic liquids in deep desulfurization of fuel", Petrochemical Technology, 2006, vol. 35, pp. 272-276.

Nie et al., "N, N-dialkylimidazolium dialkylphosphate ionic liquids: Their extractive performance for thiophene series compounds from fuel oils versus the length of alkyl group", Fuel Processing Technology, 2008, vol. 89, pp. 978-983.

U.S. Appl. No. 13/792,813, filed Mar. 11, 2013, Nicholas et al.
U.S. Appl. No. 13/714,486, filed Dec. 14, 2012, Nicholas et al.
U.S. Appl. No. 13/714,539, filed Dec. 14, 2012, Nicholas et al.
U.S. Appl. No. 13/714,528, filed Dec. 14, 2012, Nicholas et al.
U.S. Appl. No. 13/714,504, filed Dec. 14, 2012, Nicholas et al.
U.S. Appl. No. 13/793,047, filed Mar. 11, 2013, Miller et al.
U.S. Appl. No. 13/793,105, filed Mar. 11, 2013, Miller et al.
U.S. Appl. No. 13/714,493, filed Dec. 14, 2012, Nicholas et al.
U.S. Appl. No. 13/743,715, filed Jan. 17, 2013, Nicholas et al.
U.S. Appl. No. 13/792,879, filed Mar. 11, 2013, Nicholas et al.
U.S. Appl. No. 13/792,610, filed Mar. 11, 2013, Nicholas et al.

* cited by examiner

AROMATIC TRANSALKYLATION USING UZM-44 ALUMINOSILICATE ZEOLITE

FIELD OF THE INVENTION

This invention relates to a new family of aluminosilicate zeolites designated UZM-44 as the catalytic composite for aromatic transalkylation reactions. They are represented by the empirical formula of:

$$Na_n M_m^{k+} T_r Al_{1-x} E_x Si_y O_z$$

where M represents a metal or metals from zinc or Group 1 (IUPAC 1), Group 2 (IUPAC 2), Group 3 (IUPAC 3) or the lanthanide series of the periodic table, T is the organic directing agent or agents derived from reactants R and Q where R is an A,Ω-dihalosubstituted alkane such as 1,5-dibromopentane and Q is at least one neutral amine having 6 or fewer carbon atoms such as 1-methylpyrrolidine. E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

A particular zeolite, IM-5, was first disclosed by Benazzi, et al. in 1996 (FR96/12873; WO98/17581) who describe the synthesis of IM-5 from the flexible dicationic structure directing agent, 1,5-bis(N-methylpyrrolidinium)pentane dibromide or 1,6-bis(N-methylpyrrolidinium)hexane dibromide in the presence of sodium. After the structure of IM-5 was solved by Baerlocher et al. (Science, 2007, 315, 113-6), the International Zeolite Structure Commission gave the code of IMF to this zeolite structure type, see Atlas of Zeolite Framework Types. The IMF structure type was found to contain three mutually orthogonal sets of channels in which each channel is defined by a 10-membered ring of tetrahedrally coordinated atoms, however, connectivity in the third dimension is interrupted every 2.5 nm, therefore diffusion is somewhat limited. In addition, multiple different sizes of 10-membered ring channels exist in the structure.

Applicants have successfully prepared a new family of materials designated UZM-44. The topology of the materials is similar to that observed for IM-5. The materials are prepared via the use of a mixture of simple commercially available structure directing agents, such as 1,5-dibromopentane and 1-methylpyrrolidine. UZM-44 may be used as a catalyst in aromatic transalkylation reactions.

SUMMARY OF THE INVENTION

As stated, the present invention relates to using a new catalytic composite comprising a new aluminosilicate zeolite designated UZM-44 in a process for aromatic transalkylation. Accordingly, one embodiment of the invention is a material having a three-dimensional framework of at least $AlO_2$ and $SiO_2$ tetrahedral units and an empirical composition in the as synthesized and anhydrous basis expressed by an empirical formula of:

$$Na_n M_m^{k+} T_r Al_{1-x} E_x Si_y O_z$$

where "n" is the mole ratio of Na to (Al+E) and has a value from approximately 0.05 to 0.5, M represents at least one metal selected from the group consisting of zinc, Group 1 (IUPAC 1), Group 2 (IUPAC 2), Group 3 (IUPAC 3), and the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from about 0.5 to about 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

Another embodiment of the catalytic composite of the invention is a microporous crystalline zeolite having a three-dimensional framework of at least $AlO_2$ and $SiO_2$ tetrahedral units and an empirical composition in the as synthesized and anhydrous basis expressed by an empirical formula of:

$$Na_n M_m^{k+} T_r Al_{1-x} E_x Si_y O_z$$

where "n" is the mole ratio of Na to (Al+E) and has a value from approximately 0.05 to 0.5, M represents a metal or metals from Group 1 (IUPAC 1), Group 2 (IUPAC 2), Group 3 (IUPAC 3), the lanthanide series of the periodic table or zinc, "m" is the mole ratio of M to (Al+E) and has a value from 0 to 0.5, "k" is the average charge of the metal or metals M, T is the organic structure directing agent or agents derived from reactants R and Q where R is an AP-dihalogen substituted alkane having 5 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

and the zeolite is characterized in that it has the x-ray diffraction pattern having at least the d-spacings and intensities set forth in Table A. The zeolite is thermally stable up to a temperature of greater than 600° C. in one embodiment and at least 800° C. in another embodiment.

The catalytic composite of the invention may be prepared by a process comprising forming a reaction mixture containing reactive sources of Na, R, Q, Al, Si and optionally E and/or M and heating the reaction mixture at a temperature of about 160° C. to about 180° C., or about 165° C. to about 175° C., for a time sufficient to form the zeolite. The reaction mixture has a composition expressed in terms of mole ratios of the oxides of:

$$a\text{-}b\text{Na}_2\text{O}\text{:}b\text{M}_{n/2}\text{O}\text{:}c\text{RO}\text{:}d\text{Q}\text{:}1\text{-}e\text{Al}_2\text{O}_3\text{:}e\text{E}_2\text{O}_3\text{:}f\text{SiO}_2\text{:}g\text{H}_2\text{O}$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. With this number of reactive reagent sources, many orders of addition can be envisioned. Typically, the aluminum reagent is dissolved in the sodium hydroxide prior to adding the silica reagents. Reagents R and Q can be added together or separately in many different orders of addition.

The invention uses UZM-44 as the catalyst or a catalyst component in a process for the transalkylation of alkylaromatic hydrocarbons. Accordingly, a broad embodiment of the present invention is a process for transalkylation of a feedstream comprising one or more of $C_7$, $C_9$, $C_{10}$ and $C_{11}+$ aromatics to obtain a transalkylation product stream having an increased concentration of $C_8$ aromatics relative to that of the feedstream, comprising contacting the feedstream at transalkylation conditions with a catalyst comprising UZM-44.

DETAILED DESCRIPTION OF THE INVENTION

Figure 1:
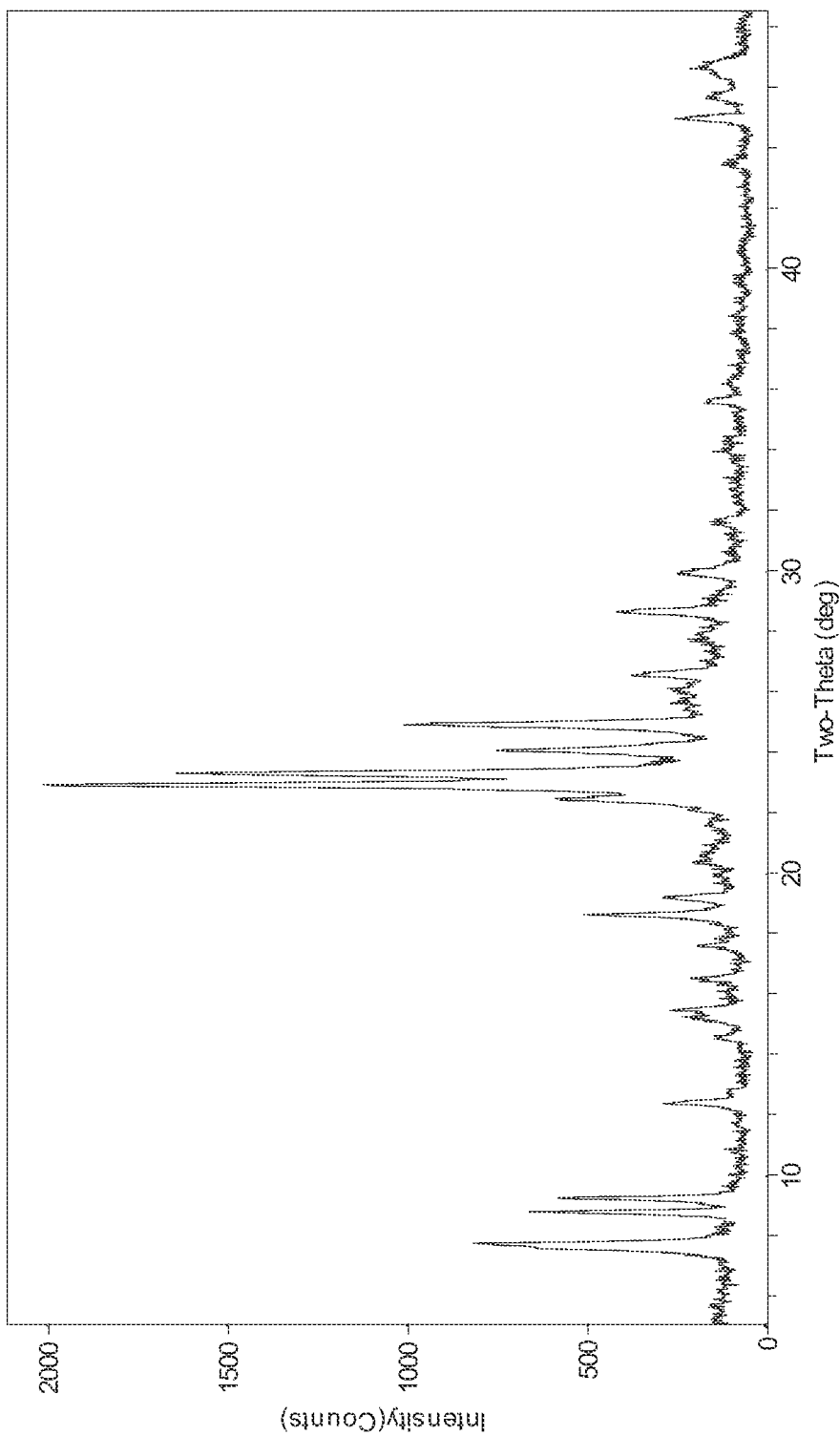
FIG. 1 is an XRD pattern of the UZM-44 zeolite formed in Example 1. This pattern shows the UZM-44 zeolite in the as-synthesized form.
Figure 2:
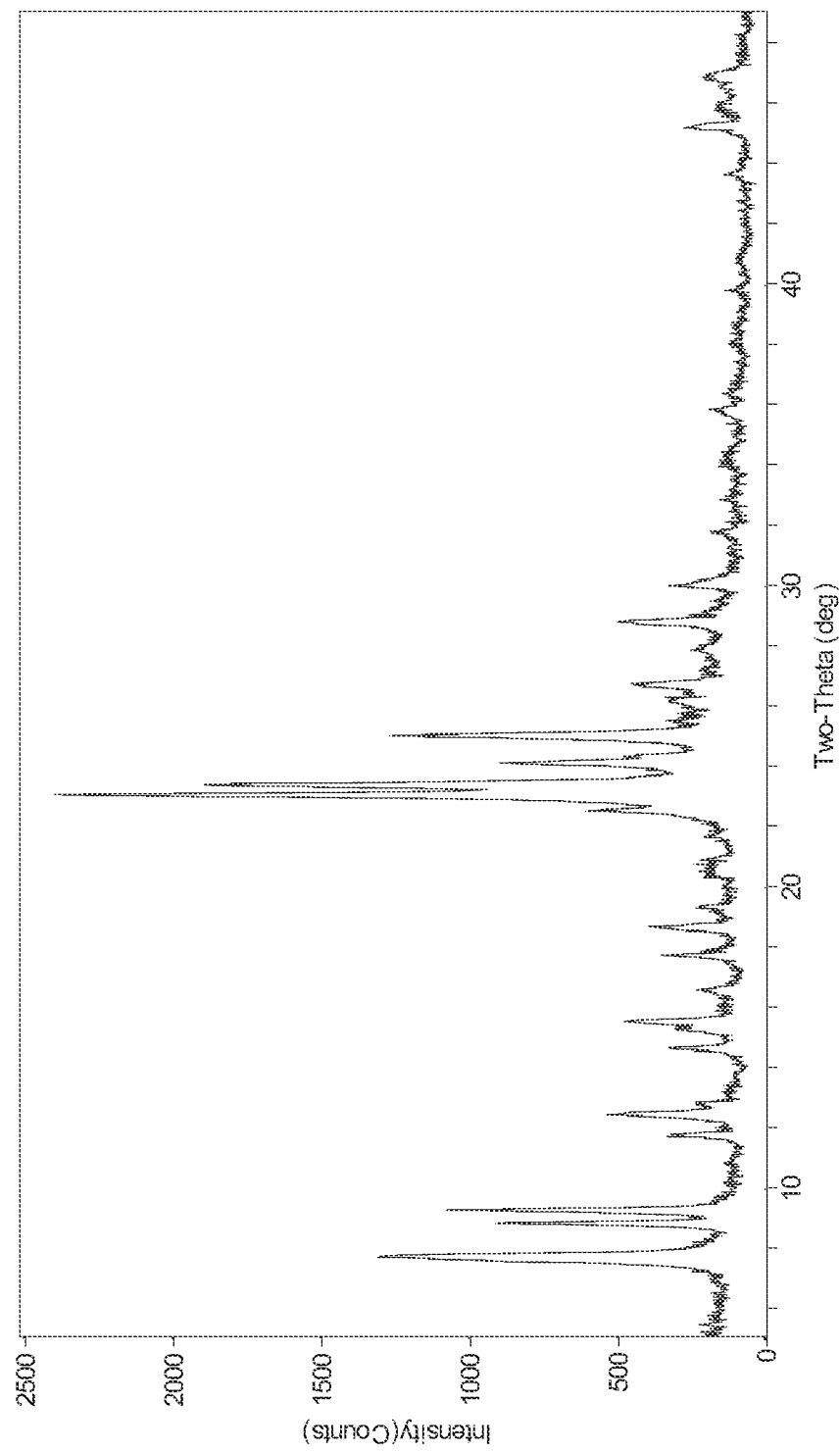
FIG. 2 is also an XRD pattern of the UZM-44 zeolite formed in Example 1. This pattern shows the UZM-44 zeolite in the $H^+$ form.

Applicants have prepared a catalytic component suitable for catalyzing aromatic transalkylation reactions where the catalytic component is an aluminosilicate zeolite whose topological structure is related to IMF as described in Atlas of Zeolite Framework Types, which is maintained by the International Zeolite Association Structure Commission at http://www.iza-structure.org/databases/, the member of which has been designated IM-5. As will be shown in detail, UZM-44 is different from IM-5 in a number of its characteristics including its micropore volume. The instant microporous crystalline zeolite, UZM-44, has an empirical composition in the as synthesized and anhydrous basis expressed by an empirical formula of:

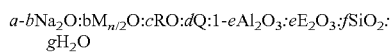

where "n" is the mole ratio of Na to (Al+E) and has a value from approximately 0.05 to 0.5, M in represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k\cdot m+3+4\cdot y)/2$$

where M is only one metal, then the weighted average valence is the valence of that one metal, i.e. +1 or +2. However, when more than one M metal is present, the total amount of:

$$M_m^{k+}=M_{m1}^{(k1)+}+M_{m2}^{(k2)+}+M_{m3}^{(k3)+}+M_{m4}^{(k4)+}+\ldots$$

and the weighted average valence "k" is given by the equation:

$$k=\frac{m1\cdot k1+m2\cdot k2+m3\cdot k3\ldots}{m1+m2+m3\ldots}$$

In one embodiment, the microporous crystalline zeolite, UZM-44, is synthesized by a hydrothermal crystallization of a reaction mixture prepared by combining reactive sources of sodium, organic structure directing agent or agents T, aluminum, silicon, and optionally E, M, or both. The reaction mixture does not comprise seeds of a layered material L. The sources of aluminum include but are not limited to aluminum alkoxides, precipitated aluminas, aluminum metal, aluminum hydroxide, sodium aluminate, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, precipitated silica and alkali silicates. Sources of sodium include but are not limited to sodium hydroxide, sodium bromide, sodium aluminate, and sodium silicate.

T is the organic structure directing agent or agents derived from reactants R and Q where R is an A,Ω-dihalogen substituted alkane having 5 carbon atoms and Q comprises at least one neutral monoamine having 6 or fewer carbon atoms. R may be an A,Ω-dihalogen substituted alkane having 5 carbon atoms selected from the group consisting of 1,5-dichloropentane, 1,5-dibromopentane, 1,5-diiodopentane, and combinations thereof. Q comprises at least one neutral monoamine having 6 or fewer carbon atoms such as 1-ethylpyrrolidine, 1-methylpyrrolidine, 1-ethylazetidine, 1-methylazetidine, triethylamine, diethylmethylamine, dimethylethylamine, trimethylamine, dimethylbutylamine, dimethylpropylamine, dimethylisopropylamine, methylethylpropylamine, methylethylisopropylamine, dipropylamine, diisopropylamine, cyclopentylamine, methylcyclopentylamine, hexamethyleneimine. Q may comprise combinations of multiple neutral monoamines having 6 or fewer carbon atoms.

M represents at least one exchangeable cation of a metal or metals from Group 1 (IUPAC 1), Group 2 (IUPAC 2), Group 3 (IUPAC 3) or the lanthanide series of the periodic table and or zinc. Specific examples of M include but are not limited to lithium, potassium, rubidium, cesium, magnesium, calcium, strontium, barium, zinc, yttrium, lanthanum, gadolinium, and mixtures thereof. Reactive sources of M include, but are not limited to, the group consisting of halide, nitrate, sulfate, hydroxide, or acetate salts. E is an element selected from the group consisting of gallium, iron, boron and combinations thereof, and suitable reactive sources include, but are not limited to, boric acid, gallium oxyhydroxide, gallium nitrate, gallium sulfate, ferric nitrate, ferric sulfate, ferric chloride and mixtures thereof.

The reaction mixture containing reactive sources of the desired components can be described in terms of molar ratios of the oxides by the formula:

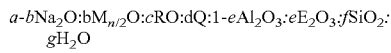

$$a\text{-}b\mathrm{Na_2O}{:}b\mathrm{M}_{n/2}\mathrm{O}{:}c\mathrm{RO}{:}d\mathrm{Q}{:}1\text{-}e\mathrm{Al_2O_3}{:}e\mathrm{E_2O_3}{:}f\mathrm{SiO_2}{:}g\mathrm{H_2O}$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. The examples demonstrate specific orders of addition for the reaction mixture which leads to UZM-44. However, as there are at least 6 starting materials, many orders of addition are possible. Also, if alkoxides are used, it is preferred to include a distillation or evaporative step to remove the alcohol hydrolysis products. While the organic structure directing agents R and Q can be added separately or together to the reaction mixture at a number of points in the process, it is preferred to mix R and Q together at room temperature and add the combined mixture to a cooled mixture of reactive Si, Al and Na sources maintained at 0-10° C. Alternatively, the mixture of R and Q, after mixing at room temperature, could be cooled and the reactive sources of Si, Al, and Na added to the organic structure directing agent mixture while maintaining a temperature of 0-10° C. In an alternative embodiment, the reagents R and Q could be added, separately or together, to the reaction mixture at room temperature.

The reaction mixture is then reacted at a temperature of about 160° C. to about 180° C., or about 165° C. to about 175° C., for a period of about 1 day to about 3 weeks and preferably for a time of about 3 days to about 14 days in a stirred, sealed reaction vessel under autogenous pressure. Static crystallization does not yield UZM-44. After crystallization is complete, the solid product is isolated from the heterogeneous mixture by means such as filtration or centrifugation, and then washed with deionized water and dried in air at ambient temperature up to about 100° C.

The as-synthesized UZM-44 is characterized by the x-ray diffraction pattern, having at least the d-spacings and relative intensities set forth in Table A below. Diffraction patterns herein were obtained using a typical laboratory powder diffractometer, utilizing the $K_\alpha$ line of copper; Cu K alpha. From the position of the diffraction peaks represented by the angle 2theta, the characteristic interplanar distances $d_{hkl}$ of the sample can be calculated using the Bragg equation. The intensity is calculated on the basis of a relative intensity scale attributing a value of 100 to the line representing the strongest peak on the X-ray diffraction pattern, and then: very weak (vw) means less than 5; weak (w) means less than 15; medium (m) means in the range 15 to 50; strong (s) means in the range 50 to 80; very strong (vs) means more than 80. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular coherently grown composite structures or for samples with crystals which are small enough to cause significant broadening of the X-rays. This can also be the case when the equipment or operating conditions used to produce the diffraction pattern differ significantly from those used in the present case.

The X-ray diffraction pattern for UZM-44 contains many peaks; an example of the x-ray diffraction patterns for an as-synthesized UZM-44 product is shown in FIG. 1. Those peaks characteristic of UZM-44 are shown in Table A. Additional peaks, particularly those of very weak intensity, may also be present. All peaks of medium or higher intensity present in UZM-44 are represented in Table A.

The zeolite may be further characterized by the x-ray diffraction pattern having at least the d-spacings and intensities set forth in Table A.

TABLE A

| 2-Theta | d(†) | I/Io % |
|---|---|---|
| 7.72 | 11.45 | m |
| 8.88 | 9.95 | m |
| 9.33 | 9.47 | m |
| 12.47 | 7.09 | w-m |
| 12.85 | 6.88 | vw |
| 14.62 | 6.05 | vw-w |
| 15.27 | 5.80 | w |
| 15.57 | 5.68 | w |
| 16.60 | 5.34 | w |
| 17.70 | 5.01 | vw-w |
| 18.71 | 4.74 | w-m |
| 19.30 | 4.59 | w |
| 22.55 | 3.94 | m |
| 23.03 | 3.86 | vs |
| 23.39 | 3.80 | s |
| 24.17 | 3.68 | m |
| 25.01 | 3.56 | m |
| 26.19 | 3.40 | vw-w |
| 26.68 | 3.34 | w-m |
| 28.76 | 3.10 | w-m |
| 30.07 | 2.97 | w |
| 35.72 | 2.51 | vw-w |
| 45.08 | 2.01 | w |
| 45.83 | 1.98 | vw-w |
| 46.77 | 1.94 | vw-w |

As will be shown in detail in the examples, the UZM-44 material is thermally stable up to a temperature of at least 600° C. and in another embodiment, up to at least 800° C. Also as shown in the examples, the UZM-44 material may have a micropore volume as a percentage of total pore volume of less than 60%.

Characterization of the UZM-44 product by high-resolution scanning electron microscopy shows that the UZM-44 forms in lathes which assemble into rectangular rod colonies.

As synthesized, the UZM-44 material will contain some exchangeable or charge balancing cations in its pores. These exchangeable cations can be exchanged for other cations, or in the case of organic cations, they can be removed by heating under controlled conditions. It is also possible to remove some organic cations from the UZM-44 zeolite directly by ion exchange. The UZM-44 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination, ion-exchange and calcination and on an anhydrous basis, the microporous crystalline zeolite UZM-44 has a three-dimensional framework of at least $AlO_2$ and $SiO_2$ tetrahedral units and an empirical composition in the hydrogen form expressed by an empirical formula of $$M1_a^{N+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z'' is the mole ratio of O to (Al+E) and has a value determined by the equation:

$$z''=(a \cdot N+3+4 \cdot y')/2$$

In the hydrogen form, after calcination, ion-exchange and calcination to remove $NH_3$, UZM-44 displays the x-ray diffraction pattern having at least the d-spacings and intensities set forth in Table B. Those peaks characteristic of UZM-44 are shown in Tables B. Additional peaks, particularly those of very weak intensity, may also be present. All peaks of medium or higher intensity present in UZM-44 are indicated in Table B.

TABLE B

| 2-Theta | d(†) | I/Io % |
|---|---|---|
| 7.71 | 11.47 | m-s |
| 8.84 | 10.00 | m-s |
| 9.24 | 9.56 | m |
| 11.76 | 7.52 | vw-w |
| 12.46 | 7.10 | m |
| 14.38 | 6.15 | vw |
| 14.64 | 6.05 | w |
| 15.26 | 5.80 | w |
| 15.52 | 5.70 | w-m |
| 16.58 | 5.34 | w |
| 17.72 | 5.00 | w-m |
| 18.64 | 4.76 | w |
| 22.56 | 3.94 | w-m |
| 23.06 | 3.85 | vs |
| 23.40 | 3.80 | s |
| 24.12 | 3.69 | m |
| 25.06 | 3.55 | m |
| 26.16 | 3.40 | vw-w |
| 26.74 | 3.33 | w-m |
| 28.82 | 3.10 | w-m |
| 30.12 | 2.96 | w |
| 35.86 | 2.50 | vw-w |
| 45.32 | 2.00 | w |
| 46.05 | 1.97 | vw-w |
| 46.92 | 1.93 | vw-w |

Similar to the as-synthesized material, the modified UZM-44 materials are thermally stable up to a temperature of at least 600° C. and in another embodiment, up to at least 800° C. and may have a micropore volume as a percentage of total pore volume of less than 60%.

Figure 3:
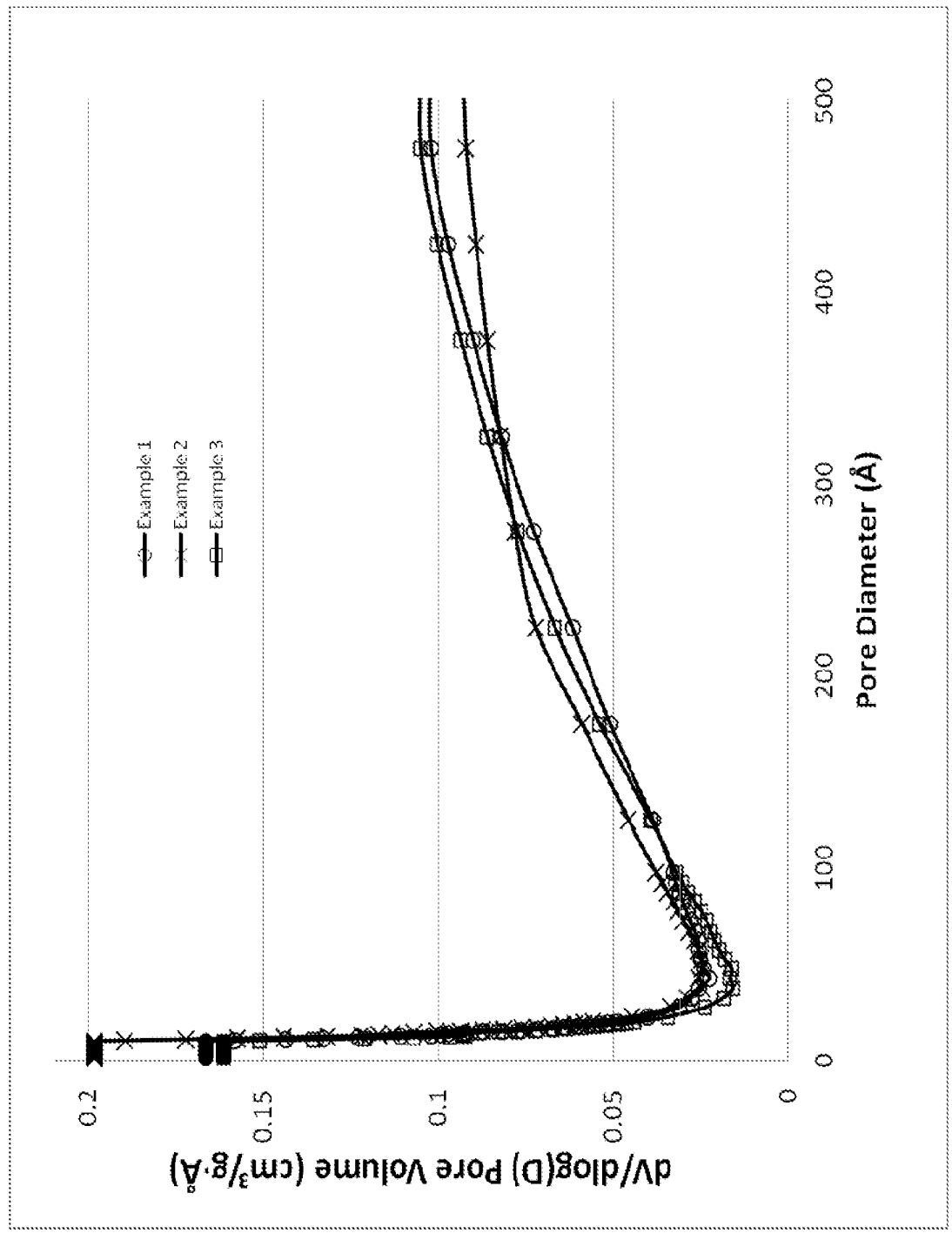
FIG. 3 is a plot derived from the $N_2$ BET experiment where dV/dlog(D) is plotted against the pore diameter. This plot shows the incremental amount of nitrogen adsorbed at each pore diameter measured.

Surface area, micropore volume and total pore volume may be determined, for example, by $N_2$ adsorption using the conventional BET method of analysis (J. Am. Chem. Soc., 1938, 60, 309-16) coupled with t-plot analysis of the adsorption isotherm as implemented in Micromeritics ASAP 2010 software. The t-plot is a mathematical representation of multilayer adsorption and allows determination of the amount of $N_2$ adsorbed in the micropores of the zeolitic material under analysis. In particular, for the materials described herein, points at 0.45, 0.50, 0.55, 0.60, and 0.65P/P$_0$ are used to determine the slope of the t-plot line, the intercept of which is the micropore volume. Total pore volume is determined at 0.98 P/P$_0$. The UZM-44 of the instant invention has a micropore volume of less than 0.155 mL/g, typically less than 0.150 mL/g and often less than 0.145 mL/g. Additionally, by looking at the dV/dlog D versus pore diameter plot (the differential volume of nitrogen adsorbed as a function of pore diameter), as shown in FIG. 3, the UZM-44 of the instant invention contains no feature at around 200-300 Å. As can be seen in FIG. 3, the material of Example 2, not in accordance with the invention, does contain an adsorption feature at around 200-300 Å. Instead, UZM-44 has an adsorption feature occurring at greater than 450 Å. In an embodiment, greater than 0.1 mL $N_2$/gÅ is differentially adsorbed at a pore diameter of 475 Å. Preferably, greater than 0.1 mL $N_2$/gÅ is differentially adsorbed at pore diameters greater than 475 Å where differentially adsorbed indicates the differential volume of nitrogen adsorbed at a particular pore diameter.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The UZM-44 zeolite and modifications thereof can also be used as a catalyst or catalyst component in catalytic composites for aromatic transalkylation processes. As used herein, the term "transalkylation" encompasses transalkylation between and among alkyl aromatics, between benzene and alkyl aromatics, and it includes dealkylation and disproportionation, e.g., of toluene to benzene and xylene. The aromatic hydrocarbons also may comprise naphthalene and other $C_{10}$ and $C_{11}$ aromatics. Herein, hydrocarbon molecules may be abbreviated $C_1, C_2, C_3, \ldots C_n$, where "n" represents the number of carbon atoms in the hydrocarbon molecule. Such abbreviations followed by a "+" is used to denote that number of carbon atoms or more per molecule, and a "−" is used to denote that number of carbon atoms or less per molecule. The UZM-44 catalyst composite may further comprise a refractory inorganic-oxide binder and a metal component. The catalyst also may be subjected to a presulfiding step to incorporate sulfur.

As stated, the zeolite as outlined above or a modification thereof, maybe in a composite with commonly known binders. The UZM-44 is used as a catalyst or catalyst support in various reactions. The UZM-44 may be mixed with a binder for convenient formation of catalyst particles in a proportion of about 5 to 100 mass % UZM-44 zeolite and 0 to 95 mass-% binder, with the UZM-44 zeolite comprising from about 5 to 100 mass-% of the composite. In one embodiment, the binder is porous, has a surface area of about 5 to about 800 m$^2$/g, and is relatively refractory to the conditions utilized in the a process. Non-limiting examples of binders are silica, aluminas, titania, zirconia, zinc oxide, magnesia, boria, thoria, chromia, stannicoxide, as well as combinations and composites thereof, for example, silica-alumina, silica-magnesia, silica-zirconia, chromia-alumina, alumina-boria, alumina-titainia, aluminophosphates, silica-zirconia, silica gel, and clays. In one embodiment the binder is one or more of amorphous silica and alumina, including gamma-, eta-, and theta-alumina. In another embodiment the binder is gamma- and or eta-alumina. Alumina may be employed as the refractory inorganic oxide for use herein, and the alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like.

The binder and zeolite may be combined in any conventional or otherwise convenient manner to form spheres, pills, pellets, granules, extrudates, or other suitable particle shape. For example, finely divided zeolite and metal salt particles can be dispersed in an alumina sol, and the mixture in turn dispersed as droplets in a hot oil bath whereby gelation occurs with the formation of spheroidal gel particles. The method is described in greater detail in U.S. Pat. No. 2,620,314. One method comprises commingling a finely divided form of the selected zeolite, refractory inorganic oxide and a metal salt with a binder and/or lubricant and compressing the mixture into pills or pellets of uniform size and shape. Alternatively, and still more preferably, the zeolite, refractory inorganic oxide and metal salt are combined and admixed with a peptizing agent in a mix-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobates, with a trilobe form being favored. The extrudates also may be formed into spheres by means of a spinning disc or drum and then dried and calcined.

In one embodiment the shapes are extrudates and or spheres. Extrudates are prepared by conventional means which involves mixing of the composition either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50 to about 200° C. and subjected to a calcination procedure at a temperature of about 450 to about 700° C. for a period of about 1 to about 20 hours. This treatment effects conversion of the hydrogel to the corresponding alumina matrix.

The catalyst of the invention optionally may comprise an additional zeolitic component. The additional zeolite component preferably is selected from one or more zeolites having the framework structure of MFI, MEL, EUO, FER, MFS, MOR, MTT, MTW, MWW, MAZ, TON and FAU (Atlas of Zeolite Framework Types) and UZM-8 as in U.S. Pat. No. 6,756,030. In one embodiment the MOR zeolite may be UZM-14 as in U.S. Pat. No. 7,687,423. In one embodiment the additional zeolitic component consists essentially of UZM-14. Suitable total zeolite amounts in the catalyst range from about 1 to about 100 wt-%, preferably from about 10 to about 95 wt-%, and more preferably between about 60 and about 90 wt-%.

The catalyst may further comprise a metal component comprising one or more elements selected from groups VIB (6), VIIB(7), VIII(8-10), 1B(11), IIB(12), IIIA(13) and IVA (14) of the Periodic Table. The metal component is selected from one or more of rhenium, nickel, cobalt, molybdenum and tungsten when the catalyst is used in a transalkylation process. The catalyst may contain phosphorus. Suitable metal amounts in the transalkylation catalyst range from about 0.01 to about 15 wt-% on an elemental basis, with the range from about 0.1 to about 12 wt-% being preferred, and the range from about 0.1 to about 10 wt-% being highly preferred. The catalyst also preferably has been subjected to a presulfiding step to incorporate from about 0.05 to about 2 wt.-% sulfur on an elemental basis. This presulfiding step may take place either during the manufacture of the catalyst or after the catalyst has been loaded into a process unit.

The finished composite may be calcined in an air atmosphere at a temperature of from about 425° to about 750° C., or in another embodiment at a temperature of from about 475° to about 6000° C., over a period of from about 0.5 to about 10 hours.

The aromatics-rich feed stream to a transalkylation or disproportionation process may be derived from a variety of sources, including without limitation catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the complex in order to remove sulfur, olefins and other compounds which would affect product quality. Light cycle oil also may be beneficially hydrocracked to yield lighter components which can be reformed catalytically to yield the aromatics-rich feed stream. If the feed stream is catalytic reformate, the reformer may be operated at high severity for high aromatics yield with a low concentration of nonaromatics in the product. The reformate also advantageously is subjected to olefin saturation to remove potential product contaminants and materials that could polymerize to heavy nonconvertibles in a transalkylation process. Such processing steps are described in U.S. Pat. No. 6,740,788 B1, hereby incorporated by reference.

The feed stream to a transalkylation or disproportionation process can be a substantially pure alkylaromatic hydrocarbon of from about 6 to about 15 carbon atoms, a mixture of such alkylaromatic hydrocarbons, or a hydrocarbon fraction rich in said alkylaromatics. The feed stream comprises alkylaromatic hydrocarbons of the general formula $C_6H_{(6-n)}R_n$, where n is an integer from 1 to 5 and R is one or more of $CH_3$, $C_2H_5$, $C_3H_7$, $C_4H_9$, or $C_5H_{11}$ in any combination. The feed stream also may comprise benzene and aromatics having from 2 to 4 rings. Suitable components of the feed stream thus generally include, for example but without so limiting the invention, benzene, toluene, ethylbenzene, meta-xylene, ortho-xylene, para-xylene, ethyl-toluenes, trimethylbenzenes, diethyl-benzenes, triethylbenzenes, propylbenzenes, methylpropylbenzenes, ethylpropylbenzenes, diisopropylbenzenes, butylbenzenes, indanes, naphthalenes, tetralins, decalins, biphenyls, diphenyls and fluorenes. The feed stream also may contain lesser concentrations of nonaromatics such as pentanes, hexanes, heptanes and heavier paraffins along with methylcyclopentane, cyclohexane and heavier naphthenes; pentanes and lighter paraffins generally will have been removed before processing in the aromatics complex. The combined transalkylation feed preferably contains no more than about 10 wt-% nonaromatics; olefins preferably are restricted to a Bromine Index of no more than about 1000, and preferably no more than about 500.

In one embodiment, a component of the feedstock is a heavy-aromatics stream comprising C9 aromatics, thereby effecting transalkylation of toluene and C9 aromatics to yield additional xylenes. Benzene may also be transalkylated to yield additional toluene. Indane may be present in the heavy-aromatics stream although it is not a desirable component to effect high yields of C8 aromatics product. In one embodiment C10+ aromatics also may be present in an amount of 30% or less of the feed. The heavy-aromatics stream preferably comprises at least about 90 mass-% aromatics, and may be derived from the same or different known refinery and petrochemical processes as the benzene and toluene feedstock and/or may be recycled from the separation of the product from transalkylation.

In one embodiment the feedstock is transalkylated in the vapor phase and in the presence of hydrogen. If transalkylated in the liquid phase, then the presence of hydrogen is optional. If present, free hydrogen is associated with the feedstock and recycled hydrocarbons in an amount of from about 0.1 moles per mole of alkylaromatics up to 10 moles per mole of alkylaromatic. This ratio of hydrogen to alkylaromatic is also referred to as hydrogen to hydrocarbon ratio. The transalkylation reaction yields a product having an increased C8 aromatics content relative to that of the feedstream. In another embodiment the transalkylation reaction also yields toluene.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stripping column in which substantially all C5 and lighter hydrocarbons present in the effluent are concentrated into an overhead stream and removed from the process. An aromatics-rich stream is recovered as net stripper bottoms, which is referred to herein as the transalkylation effluent.

The transalkylation or disproportionation reaction can be effected in contact with the catalytic composite of this invention in any conventional or otherwise convenient manner and may comprise a batch or continuous type of operation, with a continuous operation being preferred. The catalyst may be utilized as a fixed bed in a reaction zone of a vertical tubular reactor with the alkylaromatic feed stock charged through the bed in an upflow or downflow manner. Conditions employed in the transalkylation zone normally include a temperature of from about 200° to about 540° C., preferably between about 200° to about 480° C. The transalkylation zone is operated at moderately elevated pressures broadly ranging from about 100 kPa to about 6 Mpa absolute. The transalkylation reaction can be effected over a wide range of space velocities, i.e., volume of charge per volume of catalyst per hour, liquid hourly space velocity generally is in the range of from about 0.1 to about 20 hr-1.

The transalkylation effluent is separated into a light recycle stream, a mixed C8 aromatics product and a heavy-aromatics stream. The mixed C8 aromatics product can be sent for recovery of para-xylene and other valuable isomers. The light recycle stream may be diverted to other uses such as to benzene and toluene recovery, but alternatively is recycled partially to the transalkylation zone. For uses where benzene is recovered, benzene purity is of concern. Separation of benzene is usually performed by boiling point, such as in a fractionation column, so the substantial absence of compounds such as $C_6$ and $C_7$ non-aromatics with boiling points close to that of benzene in the transalkylation effluent is preferred. The benzene purity is calculated as benzene/(benzene+$C_6$ and $C_7$ non-aromatics) on a weight percent basis. In an embodiment, the benzene purity is greater than 99%, is typically greater than 99.3%, and is preferably greater than 99.5%. The heavy aromatics stream contains substantially all of the C9 and heavier aromatics and may be partially or totally recycled to the transalkylation reaction zone. In general terms, the transalkylation effluent may be separated into a benzene enriched stream and one or more remainder streams wherein the benzene enriched stream comprises at least 99.3 wt.-% benzene.

The following examples are presented in illustration of this invention and are not intended as undue limitations on the generally broad scope of the invention as set out in the appended claims.

The structure of the UZM-44 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, w and vw which represent very strong, strong, medium, weak, and very weak respectively. In terms of $100 \times I/I_o$, the above designations are defined as:

$$vw = <5; w=6-15; m=16-50; s=51-80; \text{ and } vs=80-100$$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

5.28 g of NaOH, (97%) was dissolved in 111.88 g water. 1.16 g Al(OH)$_3$, (29.32 wt.-% Al), was added to the sodium hydroxide solution. Upon the mixture becoming a solution, 33.75 g Ludox AS-40 was added and the solution was stirred vigorously for 1-2 hours and then cooled to 0° C.-4° C. Separately, 8.89 g 1,5-dibromopentane, (97%) was mixed with 9.56 g 1-methylpyrrolidine, (97%) to form a second mixture. The second mixture was added to the cooled mixture to create the final reaction mixture. The final reaction mixture was vigorously stirred and transferred to a 300 cc stirred autoclave. The final reaction mixture was digested at 170° C. for 120 hours with stirring at 100 rpm. The product was isolated by filtration. The product was identified as UZM-44 by XRD. Analytical results showed this material to have the following molar ratios, Si/Al of 11.77, Na/Al of 0.21, N/Al of 1.02, C/N of 7.75. The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 39.1% Si, 3.26% Al, 90 ppm Na with a BET surface area of 299 m$^2$/g, pore volume of 0.239 cm$^3$/g, and micropore volume of 0.139 cm$^3$/g.

Comparative Example 2

10.8 g of Aerosil 200 was added, while stirring, to a solution of 12.24 g 1,5-bis(N-methylpyrrolidinium)pentane dibromide in 114 g H$_2$O. A very thick gel was formed. Separately, a solution was made from 60 g H$_2$O, 3.69 g NaOH (99%), 0.95 g sodium aluminate (26.1% Al by analysis), and 1.86 g NaBr (99%). This second solution was added to the above mixture. The final mixture was divided equally between 7 45 cc Parr vessels. One vessel, which was digested for 12 days at 170° C. in a rotisserie oven at 15 rpm, yielded a product which was determined by XRD as having the IMF structure. The product was isolated by filtration. Analytical results showed this material to have the following molar ratios, Si/Al of 12.12, Na/Al of 0.08, N/Al of 1.03, C/N of 7.43. The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^'$ into Ht Analysis for the calcined, ion-exchanged sample shows 38.8% Si, 2.99% Al, 190 ppm Na with a BET surface area of 340 m$^2$/g, pore volume of 0.260 cm$^3$/g, and micropore volume of 0.160 cm$^3$/g.

Example 3

544 g of NaOH, (97%) was dissolved in 9.53 kg water. 118 g Al(OH)$_3$ was added to the sodium hydroxide solution while stirring. Of Ludox AS-40, 3.83 kg was added and the solution was stirred vigorously for 2 hours and then cooled to 0° C.-5° C. A solution containing 941 g H2O, 453 g 1,5-dibromopentane and 325 g N-methylpyrrolidine was added to the cooled mixture to create the final reaction mixture. The final reaction mixture was vigorously stirred and transferred to a 5 gallon stirred autoclave before digestion at 160° C. for 11 days. The product was isolated by filtration. The product was identified as UZM-44 by XRD. Analytical results showed this material to have the following molar ratios, Si/Al of 11.77, Na/Al of 0.21, N/Al of 1.02, C/N of 7.75. The product generated by this synthesis was calcined under flowing air at 600° for 6 hours. Analysis for the calcined sample shows a BET surface area of 301 m$^2$/g, pore volume of 0.238 cm$^3$/g, and micropore volume of 0.142 cm$^3$/g.

Example 4

A UZM-44 in the H+ form was loaded into a vertical steamer. The UZM-44 was exposed to 100% steam at 725° C. for 12 hours or 24 hours. The starting UZM-44 had a BET surface area of 340 m$^2$/g, pore volume of 0.301 cm$^3$/g, and micropore volume of 0.154 cm$^3$/g. After 12 hours of steaming, the UZM-44 was still identified as UZM-44 by XRD though the intensity of the first 3 peaks had increased to very strong, very strong—strong, and very strong—strong respectively. All other peaks were at positions and intensities described in Table B. The material had a BET surface area of 274 m$^2$/g, pore volume of 0.257 cm$^3$/g, and micropore volume of 0.127 cm$^3$/g. After 24 hours of steaming, the UZM-44 was still identified as UZM-44 by XRD though the intensity of the first 3 peaks had increased to very strong, very strong—strong, and very strong—strong respectively. All other peaks were at positions and intensities described in Table B. The material had a BET surface area of 276 m$^2$/g, pore volume of 0.262 cm$^3$/g, and micropore volume of 0.128 cm$^3$/g.

Example 5

UZM-44 was synthesized from a gel of composition 1 Al$_2$O$_3$: 43.6 SiO$_2$: 11.6 Na$_2$O: 6.52 1,5-dibromopentane: 18.95 N-methylpyrrolidine: 1321 H$_2$O by dissolving dissolving NaOH in water and then adding liquid sodium aluminate to the sodium hydroxide solution. Ultrasil VN3 was then added as the silica source followed by 1,5-dibromopentane and N-methylpyrrolidine to form the final reaction mixture. The final reaction mixture was vigorously stirred and transferred to a 2L stirred autoclave. The final reaction mixture was digested at 50° C. for 24 h then at 160° C. for 12 days while stirring. The product was isolated by filtration. The product was identified as UZM-44 by XRD. The product generated by this synthesis was calcined under flowing air at 600° for 6 hours. It was then ion-exchanged with 1 M ammonium nitrate solution.

Example 6

UZM-44 was synthesized from a gel of composition 1 Al$_2$O$_3$: 43.6 SiO$_2$: 11 Na$_2$O: 6.52 1,5-dibromopentane: 18.95 N-methylpyrrolidine: 900 H$_2$O by dissolving NaOH in water then adding liquid sodium aluminate to the sodium hydroxide solution. Ultrasil VN3 was then added as the silica source prior to the addition of 1,5-dibromopentane (Aldrich) and N-methylpyrrolidine (Aldrich) to form the final reaction mixture. The final reaction mixture was vigorously stirred and transferred to a 2L stirred autoclave. The final reaction mixture was digested at 50° C. overnight then at 160° C. for 9 days while stirring. The product was isolated by filtration. The product was identified as UZM-44 by XRD. Analytical results showed this material to have the following molar ratios, Si/Al of 12.14, Na/Al of 0.54, 6.95 C/N and 1.0 N/Al. The product generated by this synthesis was calcined under flowing air at 600° for 6 hours. It was then ion exchanged with 1 M ammonium nitrate solution. Analysis for the calcined, ion-exchanged sample shows a BET surface area of 327 m²/g, pore volume of 0.373 cm³/g, and micropore volume of 0.152 cm³/g.

Example 7

UZM-14 was synthesized by methods described in U.S. Pat. No. 7,687,423. After ion exchange with an ammonium nitrate solution, the zeolite was dried at a temperature of approximately 100° C. The UZM-14 was then formed into a catalyst, hereafter called Catalyst A, by blending a mixture of 75% UZM-14 and 25% peptized Catapal B boehmite with a solution of ammonium heptamolybdate to obtain a catalyst formulation with 5% molybdenum. After extrusion as 1/16" cylinders, the catalyst was calcined for 2 hours at 2 different conditions: 500° C. with 0% steam and 540° C. with 15% steam.

The UZM-44 containing catalyst, hereafter called Catalyst B, was prepared by the same procedure, with the UZM-44 of Example 6 replacing one third of the UZM-14 to obtain a catalyst with 5% Mo on a support of 50% UZM-14/25% UZM-44/25% $Al_2O_3$.

These catalysts were then used to transalkylate toluene and C9+ aromatics with a standard test protocol. The feed composition shown in Table 1 contained 75 wt % toluene and 25 wt % C9+ aromatics and the test was performed at a reactor pressure of 1725 kPa (250 psig), at weight hourly space velocity=4, and $H_2$:HC=6. The catalysts were sulfided in the test unit by doping the feed with excess dimethyl disulfide (150 ppm) for the first 40 hours of the test. The S/Mo molar ratio on the spent catalyst was typically in the 0.6-0.9 range. Data was collected at 4 different temperatures and is reported in Table 2.

TABLE 1

| Component | Weight % |
|---|---|
| Toluene | 75 |
| Propylbenzene | 2 |
| methylethylbenzene | 10 |
| trimethylbenzene | 9.7 |
| indane | 0.8 |
| methylpropylbenzene | 1.0 |
| diethylbenzene | 0.4 |
| dimethylethylbenzene | 1.0 |
| C11+ aromatics | 0.1 |

TABLE 2

| | Catalyst A 500° C., 0% stm | Catalyst B 500° C., 0% stm | Catalyst A 540° C., 15% stm | Catalyst B 540° C., 15% stm |
|---|---|---|---|---|
| Overall Conversion at 350° C. | 48.9 | 44.8 | 46.8 | 42.2 |
| Overall Conversion at 365° C. | 51.1 | 49.6 | 50.2 | 48.2 |
| Overall Conversion at 385° C. | 52.5 | 52.0 | 51.9 | 51.5 |
| Overall Conversion at 405° C. | 54.3 | 53.5 | 53.4 | 53.2 |
| Benzene Purity at 350° C. (wt %) | 99.34 | 99.41 | 99.08 | 99.38 |
| Benzene Purity at 365° C. (wt %) | 99.42 | 99.54 | 99.13 | 99.56 |
| Benzene Purity at 385° C. (wt %) | 99.60 | 99.74 | 99.35 | 99.75 |
| Benzene Purity at 405° C. (wt %) | 99.74 | 99.84 | 99.57 | 99.84 |

TABLE 2-continued

| | Catalyst A 500° C., 0% stm | Catalyst B 500° C., 0% stm | Catalyst A 540° C., 15% stm | Catalyst B 540° C., 15% stm |
|---|---|---|---|---|
| Methylethylbenzene Conv. at 350° C. | 80.4 | 88.0 | 74.4 | 89.4 |
| Methylethylbenzene Conv. at 365° C. | 91.5 | 95.9 | 87.5 | 96.2 |
| Methylethylbenzene Conv. at 385° C. | 96.1 | 98.4 | 94.8 | 98.6 |
| Methylethylbenzene Conv. at 405° C. | 96.7 | 98.7 | 96.6 | 98.9 |
| Xylene Yield at 350° C. | 26.83 | 25.55 | 26.00 | 24.33 |
| Xylene Yield at 365° C. | 26.89 | 27.14 | 26.76 | 26.70 |
| Xylene Yield at 385° C. | 26.09 | 26.97 | 26.43 | 27.01 |
| Xylene Yield at 405° C. | 24.53 | 25.71 | 25.18 | 26.08 |

Figure 4:
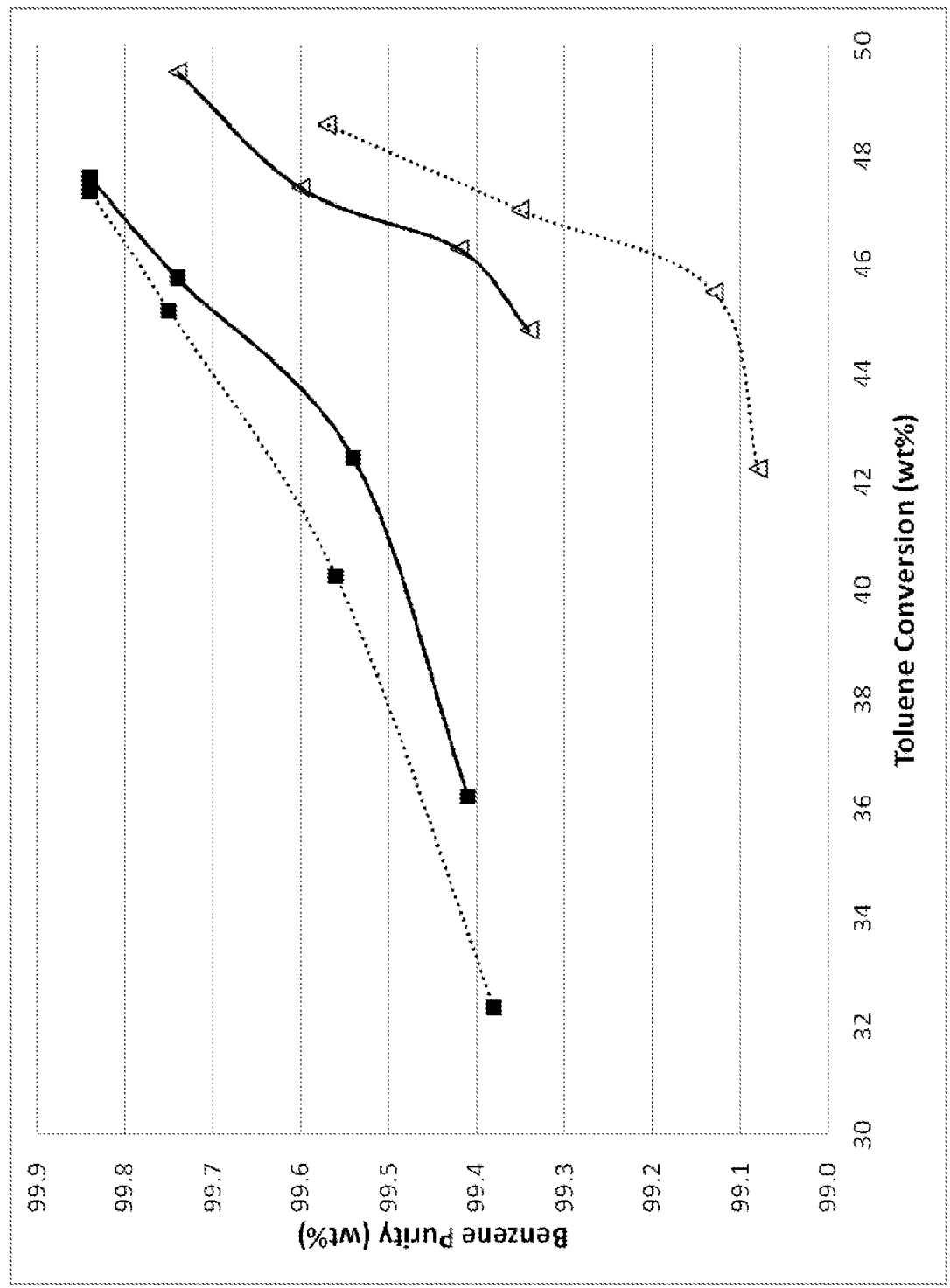
FIG. 4 is a plot of benzene purity as a function of toluene conversion over catalysts with and without UZM-44 in the catalyst composite.

FIG. 4 shows a plot of benzene purity as a function of toluene conversion for Catalyst A (open triangles) and Catalyst B (closed squares) at the two calcinations, 500° C. and 0% steam (solid lines) and 540° C. and 15% steam (dotted lines). As can be seen from the examples, the catalysts containing UZM-44 in the catalytic composite with UZM-14 have increased conversion of methylethylbenzene (MEB), higher xylene yield at equivalent conversion levels, and improved benzene purity at equivalent conversion levels.

Example 8

250 mg of $H^+$-UZM-44 was pressed and sieved to 40-60 mesh before loading into a catalytic test apparatus. The catalytic composite was heated under $N_2$ flow of 50 mL/min to 550° C. and held for 60 min. The apparatus was then cooled to 400° C. before the feed was switched from $N_2$ to $N_2$ saturated with toluene at the same flow rate. Toluene transalkylation was performed at temperatures ranging from 400° C. to 550° C. The experiment was then repeated with an MFI zeolite with $SiO_2/Al_2O_3$ mole ratio equal to 38.

TABLE 3

| Temperature | UZM-44 Xylene Yield | MFI Xylene Yield |
|---|---|---|
| 400° C. | 12.9 | 1.9 |
| 425° C. | | 2.1 |
| 450° C. | 15.5 | 2.5 |
| 475° C. | | 3.6 |
| 500° C. | 18.4 | 5.2 |
| 550° C. | 19.2 | |

The invention claimed is:

1. A process for transalkylation of a feedstream comprising contacting the feedstream comprising one or more of $C_7$, $C_9$, $C_{10}$ and $C_{11}$+ aromatics to produce a transalkylation product stream having an increased concentration of $C_8$ aromatics relative to that of the feedstream, at transalkylation conditions with a catalytic comprising a first microporous crystalline zeolite, UZM-44, having a three-dimensional framework of at least $AlO_2$ and $SiO_2$ tetrahedral units and an empirical composition in the as synthesized and anhydrous basis expressed by an empirical formula of:

where "n" is the mole ratio of Na to (Al+E) and has a value from approximately 0.05 to 0.5, M represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of 0 to (Al+E) and has a value determined by the equation:

$z = (n + k \cdot m + 3 + 4 \cdot y)/2;$ wherein the macroporous crystalline zeolite, UZM-44, is further characterized in that it has the x-ray diffraction pattern having at least the d-spacings and intensities set forth in Table A:

TABLE A

| 2-Theta | d(Å) | I/Io % |
|---|---|---|
| 7.72 | 11.45 | m |
| 8.88 | 9.95 | m |
| 9.33 | 9.47 | m |
| 12.47 | 7.09 | w-m |
| 12.85 | 6.88 | vw |
| 14.62 | 6.05 | vw-w |
| 15.27 | 5.80 | w |
| 15.57 | 5.68 | w |
| 16.60 | 5.34 | w |
| 17.70 | 5.01 | vw-w |
| 18.71 | 4.74 | w-m |
| 19.30 | 4.59 | w |
| 22.55 | 3.94 | m |
| 23.03 | 3.86 | vs |
| 23.39 | 3.80 | s |
| 24.17 | 3.68 | m |
| 25.01 | 3.56 | m |
| 26.19 | 3.40 | vw-w |
| 26.68 | 3.34 | w-m |
| 28.76 | 3.10 | w-m |
| 30.07 | 2.97 | w |
| 35.72 | 2.51 | vw-w |
| 45.08 | 2.01 | w |
| 45.83 | 1.98 | vw-w |
| 46.77 | 1.94 | vw-w. |

2. The process of claim 1 wherein the catalytic composite is thermally stable up to a temperature of greater than 600° C.

3. The process of claim 1 wherein the catalytic composite has a micropore volume as a percentage of total pore volume of less than 60%.

4. The process of claim 1 wherein the catalytic composite has a micropore volume of less than 0.155 mL/g.

5. The process of claim 1 wherein the catalytic composite has a micropore volume of less than 0.150 mL/g.

6. The process of claim 1 wherein the catalytic composite exhibits no feature at 200-300 Å on a dV/dlog D versus pore diameter plot of differential volume of nitrogen adsorbed as a function of pore diameter.

7. The process of claim 1 wherein the zeolite exhibits an adsorption feature occurring at greater than 450 Å on a dV/dlog D versus pore diameter plot of differential volume of nitrogen adsorbed as a function of pore diameter.

8. The process of claim 1 wherein the differential volume of nitrogen adsorbed by the zeolite at a pore diameter of 475 Å is greater than 00.1 mL $N_2$/gÅ on a dV/dlog D versus pore diameter plot of differential volume of nitrogen adsorbed as a function of pore diameter.

9. The process of claim 1 wherein the differential volume of nitrogen adsorbed by the zeolite at pore diameters greater than 475 Å is greater than 0.1 mL $N_2$/gÅ on a dV/dlog D versus pore diameter plot of differential volume of nitrogen adsorbed as a function of pore diameter.

10. The process of claim 1 wherein the feedstream further comprises further comprises a component selected from the group consisting of benzene, $C_8$ aromatics, aromatic compounds having from 2 to 4 rings, and combinations thereof.

11. The process of claim 1 wherein the feedstream further comprises a bottoms stream from a fractionation of $C_8$ aromatics from the transalkylation product stream.

12. The process of claim 1 wherein the transalkylation conditions comprise a temperature from about 200° C. to about 540° C., a pressure from about 100 kPa to about 6 MPa absolute, and a space velocity from about 0.1 to about 20 $hr^{-1}$.

13. The process of claim 1 wherein the catalytic composite is located in one or more catalyst zones arranged in series or parallel configuration, and wherein the catalytic composite may be in fixed beds or fluidized beds.

14. The process of claim 1 wherein the catalytic composite further comprises a zeolite having the framework structure MOR.

15. The process of claim 1 wherein the catalytic composite further comprises UZM-14.

16. The process of claim 1 wherein the transalkylation product stream is separated into a benzene-enriched stream comprising at least 99.3 wt.-% benzene and at least one remainder stream.

17. The process of claim 1 wherein the transalkylation product stream is separated into a benzene-enriched stream comprising at least 99.5 wt.-% benzene and at least one remainder stream.

* * * * *

UNITED STATES PATENT AND TRADEMARK OFFICE
CERTIFICATE OF CORRECTION

PATENT NO. : 8,609,921 B1  
APPLICATION NO. : 13/792667  
DATED : December 17, 2013  
INVENTOR(S) : Christopher P. Nicholas et al.

Page 1 of 1

It is certified that error appears in the above-identified patent and that said Letters Patent is hereby corrected as shown below:

In the Claims

Column 16,

Line 58, after "with a catalytic" insert --composite--.

Column 17,

Line 19, replace "macroporous" with --microporous--.

Signed and Sealed this
Second Day of June, 2015

Michelle K. Lee
*Director of the United States Patent and Trademark Office*